United States Patent [19]

Goodman et al.

[11] Patent Number: 4,506,010

[45] Date of Patent: Mar. 19, 1985

[54] METHOD FOR TESTING MICROBIAL DEGRADATION OF CELLULOSE

[75] Inventors: Nelson Goodman; Brian C. Cunningham, El Cerrito, Calif.

[73] Assignee: Stauffer Chemical Company, Westport, Conn.

[21] Appl. No.: 330,640

[22] Filed: Dec. 14, 1981

Related U.S. Application Data

[63] Continuation of Ser. No. 237,004, Feb. 23, 1981, abandoned.

[51] Int. Cl.³ .............. C12Q 1/18; C12Q 1/06; C12Q 1/04; C12P 19/14
[52] U.S. Cl. .................... 435/32; 435/34; 435/39; 435/99
[58] Field of Search ............ 435/18, 19, 22, 29, 435/32, 33, 34, 39, 400, 911, 945, 99

[56] References Cited

U.S. PATENT DOCUMENTS 3,509,026  4/1970  Sanders ........................... 435/33
3,957,583  5/1976  Gibson et al. ................... 435/33
4,036,697  7/1977  Pierre et al. ................... 435/22 X

OTHER PUBLICATIONS

Thomas E. Barman, Enzyme Handbook, vol. II, pp. 560, 561, 565 and 566; 1969.

E. Grossbard and G. I. Wingfield, "The Effect of Herbicides on Cellulose Decomposition", Herbicides and Soil Microflora; pp. 236–253.

Primary Examiner—David M. Naff
Attorney, Agent, or Firm—Michael J. Bradley

[57] ABSTRACT

Changes in the optical density and viscosity measurements of a water-soluble cellulose derivative which is enzyme depolymerizable can be used as a method to determine growth of cellulase-producing microorganisms and cellulose degradation. The method is particularly well suited to the measurement of the effect of pesticides on cellulose degradation.

2 Claims, No Drawings

METHOD FOR TESTING MICROBIAL DEGRADATION OF CELLULOSE

This is a continuation of application Ser. No. 237,004, filed Feb. 23, 1981, now abandoned.

BACKGROUND OF THE INVENTION

The Environmental Protection Agency requires data on pesticidal effects upon microbial growth and function to support registration of a pesticide for commercial application. The growth of cellulase-producing microorganisms which degrade cellulose is particularly important for the eco-system. Therefore, a need exists for an accurate and economical method for testing a pesticide's potential inhibition of cellulase activity and cellulose degradation.

PRIOR ART

Several techniques have been developed for measuring cellulose degradation. One method involved the use of dye indicators. Cellulolytic fungi uncoupled blue dye from dye-bound cellulose powder during incubation, and the free dye diffused into the basal layer of medium. The amount of dye released, and the speed of release, appeared related to the degree of cellulolytic ability of individual cultures. See R. E. Smith, "Rapid Tube Test for Detecting Fungal Cellulase Production," 33 *Applied and Environmental Microbiology* 980 (1977).

Another method involved measurement of the depth of clearing of opaque columns of an agar medium containing a partially crystalline cellulose preparation inoculated with fungi. As the organisms grew, they secreted cellulolytic enzymes which hydrolyzed the cellulose substrate. This created a sharply defined clear zone in the opaque medium beneath the growing culture. See G. S. Rautela and E. G. Cowling, "Simple Cultural Test for Relative Cellulolytic Activity of Fungi," 14 *Applied Microbiology* 892 (1966). The method is better suited to measurement of relative activities of various fungi than to changes in the activity of a particular species under varying conditions.

Filter papers and disks have also been used to assay cellulase activity. See "Antibiotic Disks—An Improvement in the Filter Paper Assay for Cullulose," 20 *Biotechnology and Bioengineering* 297 (1978).

Common methods of measuring the cellulase inhibitory effects of herbicides have utilized the disintegration of cotton thread and calico in soil. See E. Grossbard and G. I. Wingfield, "The Effect of Herbicides on Cellulose Decomposition," *Herbicides and Soil Microflora*, 236-253. The limitation of these methods inheres in the insolubility of the cellulose which restricts quantitative measurement of its disintegration.

SUMMARY OF THE INVENTION

This invention provides a quantitative method for measuring growth of cellulase-producing microorganisms and degradation of cellulose. The method utilizes a water soluble cellulose derivative to measure microbial cellulose degradation as a reduction in viscosity. The method is particularly suited to testing the effect of pesticides on microbial growth and function.

DESCRIPTION OF THE INVENTION

This invention relates to a method for measuring the growth of cellulase-producing microorganisms and degradation of cellulose. It is superior to previous methods because it provides for precise quantitative measurement.

The cellulose component used in the method of this invention must be a water-soluble colloidal cellulose derivative. It is used as a growth medium when supplied with nutrients and inoculated with a cellulase-producing microorganism. Growth of the microorganism or cellulase production is determined by measuring increases in the optical density of the medium. Microbial cellulose degradation is measured by reductions in viscosity.

Although any water-soluble colloidal cellulose derivative, which is enzyme depolymerizable, may be used as a growth medium, the method was tested using cellulose sulfate ester derivatives. These cellulose derivatives and their preparation are described in U.S. Pat. Nos. 3,702,843 and 4,141,746, and an article by Richard G. Schweiger, "New Cellulose Sulfate Derivatives and Applications," 70 *Carbohydrate Research* 185-198 (1979).

The sulfate ester groups of this cellulose derivative are homogeneously distributed among the polymer units. Preferably, the degree of substitution is less than one. When the degree of substitution is greater than one, the sulfates are relatively resistant to enzyme degradation.

Since the viscous properties of the cellulose are critical to the method of this invention, it may be noted that the colloidal cellulose sulfate esters used herein were viscous at 1.0% of an aqueous solution. Reductions in viscosity during cellulose degradation can be quantitatively measured with a viscoso-meter.

The colloidal cellulose sulfate ester derivative, described herein, can be prepared as a nutrient growth medium for the cellulase producing microorganisms as follows. An aqueous solution is prepared containing from approximately 0.1 to 10.0%, preferably 0.5 to 2.0% cellulose sulfate ester. To this solution a nutrient is added such as, from 0.01% to 20.0% yeast extract. Preferably, the yeast extract comprises between 0.1-2.0% of the solution. The solution may also contain up to 10.0%, but ideally up to 2%, 2-amino-2-hydroxymethyl-1,3-propanediol.

The medium is then inoculated with a cellulase-producing microorganism. Examples of such organisms include *Trichodema viride* and *Cellulomonas biazotea*. The latter microorganism was used to demonstrate the method of this invention.

The method of this invention for measuring the growth of the microorganism and cellulose degradation was tested according to the procedure described in Example 1. It was then tested to measure the effect of herbicides on cellulase growth and cellulose degradation as described in Examples 2 and 3.

EXAMPLE 1

An aqueous medium was prepared containing 1.21% Tris(2-amino-2-hydroxymethyl-1,3-propanediol), 0.5% yeast extract, and 1.2% colloidal cellulose sulfate ester having medium negative charge and viscosity of approximately 70-1600 cps. One-hundred milliliter (ml) portions of the medium were placed in 500 ml dented-bottomed flasks having gauze closures. The pH was adjusted to 7.5 by adding 38% hydrochloric acid.

After sterilization by autoclaving for 20 minutes, each test flask of medium was inoculated with a 1 ml cell suspension of Cellulomonas biazotea. The cultures and 6 uninoculated control flasks were incubated at 30° C. and 150 rpm.

Table I shows the viscosity and optical density measurements at 24, 48, and 72 hour intervals. Assays of the uninoculated control flasks did not indicate a significant drop in viscosity. Assays of the inoculated flasks demonstrated degradation of cellulose by *Cellulomonas biazotea* as evidenced by the concommitant decrease in viscosity. Forty-eight hours after inoculation, viscosity dropped from an average of 155 centipoise to 10 centipoise. After 54 hours it had dropped to 5 centipoise.

Density increased from 40 Klett units 24 hours after inoculation to 264 at 72 hours, indicating growth of the microorganism.

TABLE I

Colloidal Cellulose Sulfate Ester Viscosity and Optical Density

| | Hours | | | | | |
|---|---|---|---|---|---|---|
| | 0 | 24 | 30 | 48 | 54 | 72 |
| Viscosity (centipoise) | | | | | | |
| Uninoculated cellulose | 155 | — | 149 | — | 140.5 | 143 |
| Cellulose inoculated with *Cellulomonas biazotea* | — | 104 | 59 | 10 | 7 | 4 |
| Density (Klett units) | | | | | | |
| Cellulose inoculated with *Cellulomonas biazotea* | 16 | 42 | 68 | 210 | 268 | | lent to the maximum recommended 6, 12, and 60 pounds per acre (lb/A) application rates for the herbicide.

Control groups contained (1) *Cellulomonas biazotea* inoculated cellulose alone, and (2) inoculated cellulose and 2% ethanol solvent. Test and control flasks were incubated under the same conditions as in Example 1. Viscosity measurements are shown in Table II. Optical density measurements are shown in Table III. At 66 hours after incubation the control cultures containing 2% ethanol and no herbicide showed a 70% loss in viscosity and a 30 Klett unit increase in optical density, indicating normal growth and function of the cellulase-producing microorganism.

The viscosity and optical density of the test flakes containing herbicide at 6 ppm did not significantly deviate from the control group.

Cultures with 12 and 60 ppm herbicide showed a decrease in optical density and less viscosity reduction. After 66 hours, cultures with 12 ppm herbicide had a viscosity reduction of only 85% of the control level and an optical density increase of only 47% of the control level. In cultures with 60 ppm herbicide the viscosity loss was further reduced to only 32% and the increase in optical density was only 12% of the control value. The results indicate that at elevated concentration levels the herbicide was inhibiting microorganism growth and cellulase production.

TABLE II

Effect of Herbicide on Cellulose Degradation/Viscosity

| Medium | Viscosity (Centipoise)/Hours | | | | | | |
|---|---|---|---|---|---|---|---|
| | 0 | 26.5 | 42.5 | 66 | 97.5 | 118 | 139 |
| Uninoculated: | 247 | — | — | — | — | — | 184 |
| Inoculated with *Cellulomonas biazotea:* | | | | | | | |
| No additives | | 175 | 62 | 8 | — | — | — |
| 2% ethanol added | | 195 | 183 | 70 | — | — | — |
| 2% ethanol and 6ppm S—ethyl diisobutylthiocarbamate added | | 203 | 177 | 69 | 18 | 11 | — |
| 2% ethanol and 12 ppm S—ethyl diisobutylthiocarbamate added | | 205 | 180 | 97 | 30 | 15 | — |
| 2% ethanol and 60 ppm S—ethyl diisobutylthiocarbamate added | | 203 | 196 | 178 | 108 | — | 24 |

TABLE III

Effect of Herbicide on *Cellulomonas biazotea* Growth

| Medium | Optical Density/Hours | | | | | | |
|---|---|---|---|---|---|---|---|
| | 0 | 26.5 | 42.5 | 66 | 97.5 | 118 | 139 |
| Uninoculated: | 18 | — | — | — | — | — | 17 |
| Inoculated with *Cellulomonas biazotea:* | | | | | | | |
| No additives | — | 22 | 83 | 204 | — | — | — |
| 2% ethanol added | — | 19 | 20 | 50 | — | — | — |
| 2% ethanol and 6 ppm S—ethyl diisobutylthiocarbamate added | — | 17 | 19 | 49 | 114 | 142 | — |
| 2% ethanol and 12 ppm S—ethyl diisobutylthiocarbamate added | — | 19 | 23 | 33 | 75 | 118 | — |
| 2% ethanol and 60 ppm S—ethyl diisobutylthiocarbamate added | — | 20 | 18 | 22 | 26 | — | 109 |

EXAMPLE 2

The method of this invention was used to test the effect of the herbicide S-ethyl diisobutylthiocarbamate on the growth of *Cellulomonas biazotea* and subsequent cellulose degradation of the colloidal cellulose sulfate ester.

The herbicide can be prepared by the methods described in U.S. Pat. No. 2,913,327. Inoculated batchs of the cellulose sulfate ester in 2% ethanol solvent were treated with 6, 12, and 60 parts per million (ppm) of the herbicide. The concentrations were considered equiva-

EXAMPLE 3

The herbicide Naproamide, or 2-(α-naphthoxy)-N,N-diethylpropionamide, was also tested by the method of this invention to determine its effect on the growth of *Cellulomonas biazotea* and cellulose degradation. The herbicide which is commercially available as Devinol ® can be prepared by the procedures described in U.S. Pat. No. 3,480,671.

The measurements of cellulose degradation through viscosity reduction appear in Table IV. The measurements of the growth of *Cellulomonas biazotea* through optical density increases appear in Table V.

TABLE IV

EFFECT OF NAPROPAMIDE ON CELLULOSE DEGRADATION (VISCOSITY) REDUCTION BY *CELLULOMONAS BIAZOTEA* IN COLLOID X-H2 BROTH

| Colloid X-H2 Broth Additions | Replicate | Viscosity (Centipoise)/Time After Inoculation | | | | | |
|---|---|---|---|---|---|---|---|
| | | Initial | 22.5 h | 29.5 h | 45 h | 52 h | 69 h |
| Uninoculated Sterile Medium | A | 149 | — | — | — | — | 139.0 |
| 0.1% ethanol | B | 154 | — | — | — | — | 140.4 |
| Inoculated with *Cellulomonas biazotea* | A | — | 94 | 59 | 30 | 22 | 5 |
| 0.1% ethanol | B | — | 94 | 61 | 29 | 18 | 7 |
| 0.1% ethanol +3 ppm Napropamide | A | — | 109 | 59 | 29 | — | 3 |
| | B | — | 92 | 64 | 29 | — | — |
| 0.1% ethanol +6 ppm Napropamide | A | — | 93 | 64 | 29 | 19 | 2 |
| | B | — | 105 | 69 | 34 | 18 | 2 |
| 0.1% ethanol +30 ppm Napropamide | A | — | 120 | 63 | 35 | 19 | 8 |
| | B | — | 124 | 88 | 35 | 31 | — |

TABLE V

EFFECT OF NAPROPAMDE ON THE GROWTH (OPTICAL DENSITY) OF *CELLULOMONAS BIAZOTEA* IN COLLOID X-H2 BROTH

| Colloid X-H2 Broth Additions | Replicate | Klett Optical Density/Time After Inoculation | | | | | |
|---|---|---|---|---|---|---|---|
| | | Initial | 22.5 h | 29.5 h | 45 h | 52 h | 69 h |
| Uninoculated Sterile Medium | A | 20 | — | — | — | — | 20 |
| 0.1% ethanol | B | 20 | — | — | — | — | 20 |
| Inoculated with *Cellulomonas biazotea* | A | — | 65 | 120 | 220 | 230 | 250 |
| 0.1% ethanol | B | — | 65 | 110 | 230 | 236 | 250 |
| 0.1% ethanol +3 ppm Napropamide | A | — | 60 | 108 | 216 | — | 236 |
| | B | — | 63 | 101 | 218 | — | — |
| 0.1% ethanol +6 ppm Napropamide | A | — | 65 | 100 | 198 | 228 | 236 |
| | B | — | 58 | 101 | 208 | 228 | 248 |
| 0.1% ethanol +30 ppm Napropamide | A | — | 40 | 91 | 157 | 195 | 200 |
| | B | — | 48 | 66 | 150 | 195 | — |

We claim:

1. A method for measuring pesticidal effect on growth and function of cellulase-producing microorganisms which comprises
   (a) forming a mixture of water and a water-soluble colloidal cellulose derivative which is enzyme depolymerxable as a growth medium;
   (b) providing suitable nutrients to the medium to familitate microorganism growth;
   (c) inoculating the medium with a cellulase-producing microorganism;
   (d) treating separate portions of the medium with the pesticide to be tested while retaining at least one separate portion as a comparison test control;
   (e) measuring changes in optical density; and
   (f) measuring changes in the viscosity of the medium over a period of time whereby the inhibitory effects of the pesticide can be measured by observed changes in optical density and viscosity of the cellulose sulfate/water mixture portions when compared to the test control.

2. A method according to claim 1 in which the cellulose derivative is a homogeneously substituted sulfate ester having a degree of substitution of less than one.

* * * * *

UNITED STATES PATENT AND TRADEMARK OFFICE
CERTIFICATE OF CORRECTION

PATENT NO. : 4,506,010

DATED : March 19, 1985

INVENTOR(S) : Nelson Goodman, Brian C. Cunningham

It is certified that error appears in the above-identified patent and that said Letters Patent is hereby corrected as shown below:

Column 3, Table I, at line 25, entries for columns under Hours for 54 and 72 should read 219 and 268, respectively.

Signed and Sealed this

Third Day of June 1986

[SEAL]

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,506,010

DATED : March 19, 1985

INVENTOR(S) : Nelson Goodman, Brian C. Cunningham

It is certified that error appears in the above-identified patent and that said Letters Patent is hereby corrected as shown below:

In Column 3, Table I, at line 25, entries for columns under Hours for 54 and 72 should read 219 and 268, respectively.

In Column 5, line 40, "depolymerxable" should read depolymerizable.

In Column 6, line 37, "...can be measured by..." should read can be determined by...

In Column 6, lines 38-39, "...cellulose sulfate/water..." should read cellulose derivative/water...

This certificate supersedes Certificate of Correction issued June 3, 1986.

Signed and Sealed this

Fifteenth Day of July 1986

[SEAL]

Attest:

DONALD J. QUIGG

Attesting Officer

Commissioner of Patents and Trademarks